United States Patent
Hood

[19]

[11] Patent Number: 5,807,310
[45] Date of Patent: Sep. 15, 1998

[54] IRRIGATION SLEEVE FOR AN ULTRASONIC TIP

[75] Inventor: Larry L. Hood, Laguna Hills, Calif.

[73] Assignee: Nexus Medical System, Inc. LLC, Irvine, Calif.

[21] Appl. No.: 854,904

[22] Filed: May 13, 1997

[51] Int. Cl.⁶ .................................................. A61B 17/20
[52] U.S. Cl. ............................................. 604/22; 606/107
[58] Field of Search .............................. 604/22, 35, 264; 606/107, 128, 169, 171

[56] References Cited

U.S. PATENT DOCUMENTS

| | | | |
|---|---|---|---|
| 4,808,154 | 2/1989 | Freeman | 604/22 |
| 5,084,009 | 1/1992 | Mackool | 604/22 |
| 5,188,589 | 2/1993 | Wypych et al. | 604/22 |
| 5,199,943 | 4/1993 | Wypych | 604/22 |
| 5,282,786 | 2/1994 | Ureche | 604/22 |
| 5,354,265 | 10/1994 | Mackool | 604/22 |

*Primary Examiner*—Michael Powell Buiz
*Assistant Examiner*—David O. Reip
*Attorney, Agent, or Firm*—Blakely Sokoloff Taylor & Zafman

[57] ABSTRACT

An irrigation sleeve for a surgical instrument which has an outer band that is attached to the sleeve. The irrigation sleeve has an inner bore that extends from a proximal end to a distal end of the sleeve. Located at the distal end of the sleeve is a tip which has an outlet port. The outer band is attached to the distal end of the sleeve at a location that is adjacent to the tip. The sleeve is typically constructed from a silicone rubber material that is flexible enough so that the tip can be repeatedly inserted through an incision in a cornea without damaging the eye. The band is preferably constructed from a rigid material such as TEFLON which will not collapse when inserted through the cornea incision. The band has a low coefficient of thermal conductivity so that heat is not transferred to the cornea tissue. The band also has a low coefficient of friction so that the Decemets membrane does not roll up on the sleeve when inserted into and out of the incision.

12 Claims, 2 Drawing Sheets

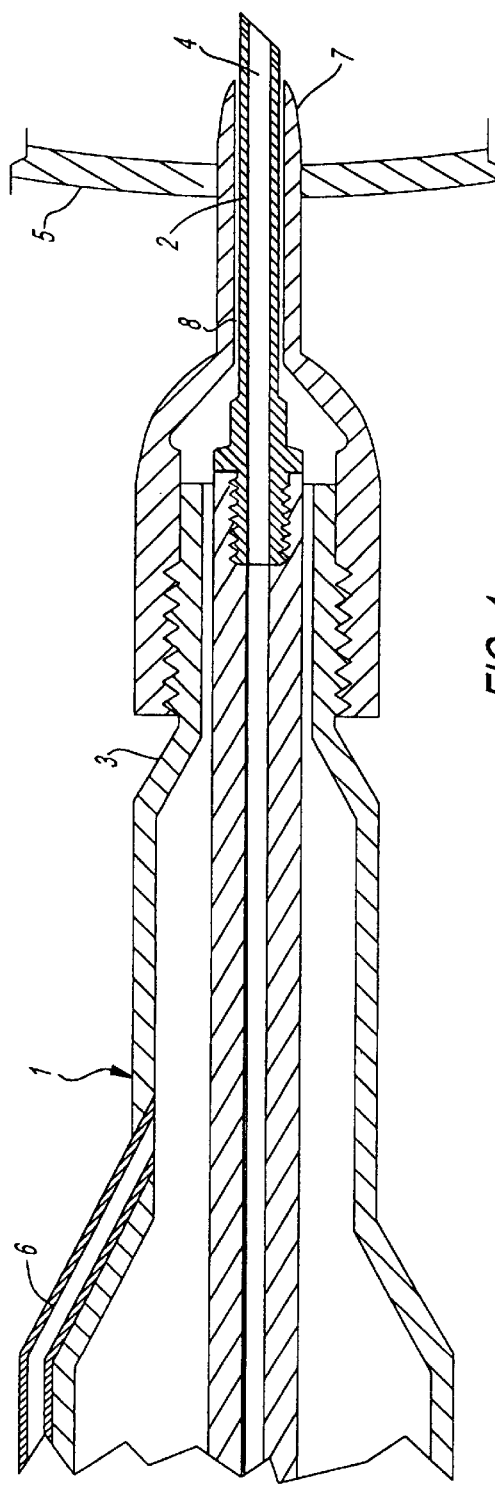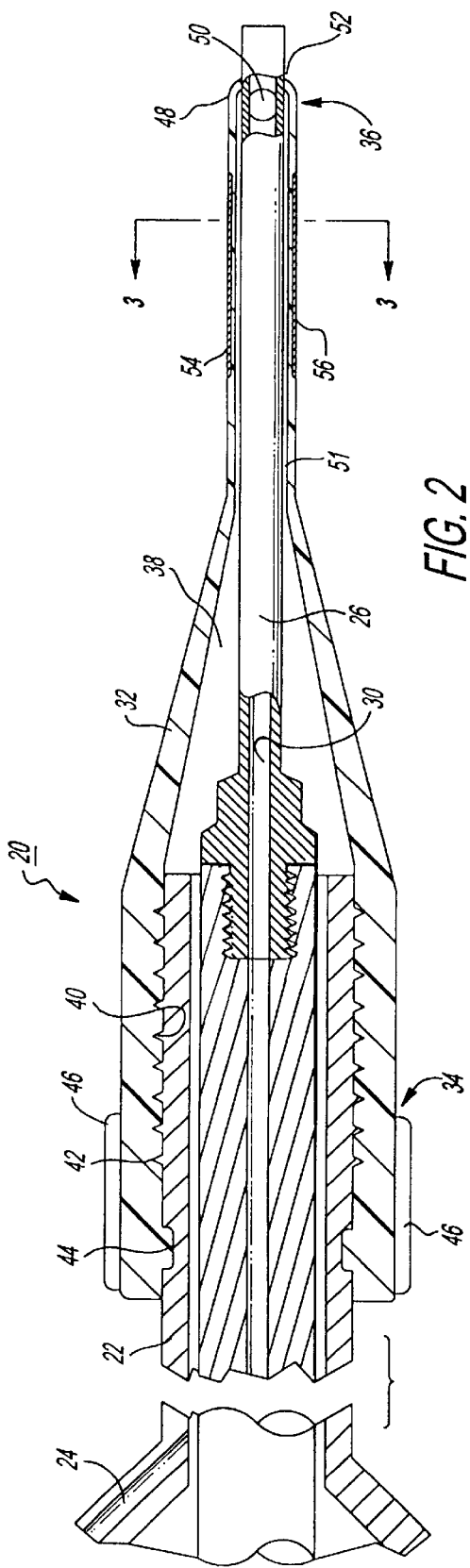

1

IRRIGATION SLEEVE FOR AN ULTRASONIC TIP

BACKGROUND OF THE INVENTION

1. Field of the Invention

The present invention relates to an irrigation sleeve for an ultrasonically driven surgical instrument.

2. Description of Related Art

The lens of a human eye may fail to properly function thereby impairing the vision of a patient. A technique commonly referred to as phacoemulsification ("phaco") can be performed to replace the disfunctional lens. A phaco procedure includes the steps of making an incision in the cornea and inserting a tip that will break and remove the lens. The tip is typically driven by an ultrasonic device which imparts a vibratory energy to the lens. The tip is part of a surgical instrument that is coupled to an irrigation line and an aspiration system. The irrigation line provides an irrigation fluid to the anterior chamber of the cornea. The aspiration system pulls the irrigation fluid and emulsified lens from the cornea.

FIG. 1 shows a typical surgical instrument 1 used to perform phaco procedures. The surgical instrument 1 includes an outer irrigation sleeve 2 that is attached to an outer shell 3 of the instrument 1. An ultrasonically driven tip 4 extends through the shell 3 and the sleeve 2. The vibrating tip 4 emulsifies the lens of the cornea 5.

The shell 3 has an irrigation inlet port 6 that is connected to an irrigation line. The irrigation line provides an irrigation fluid to the instrument. The sleeve 2 has an outlet port 7 that allows the irrigation fluid to flow into the eye. The diameter of the tip 4 is smaller than the diameter of the shell 3 and sleeve 2 to provide a passage 8 that allows the irrigation fluid to flow from the inlet port 6 to the outlet port 7.

The tool 4 and sleeve 2 may be inserted into and pulled out of the incision many times during a phaco procedure. When inserting the tool 4 and sleeve 2 into the cornea it is desirable to prevent any tearing of the incision. To date most sleeves 2 have been constructed from a flexible silicone rubber material which is flexible enough to slide through the incision without damaging the cornea. Unfortunately, the rubber material has a relatively high coefficient of friction which may induce a rolling up of Decemets membrane.

The irrigation fluid must be provided at a sufficient pressure and flowrate to maintain the interocular pressure of the cornea without damaging corneal tissue. It is desirable to provide an incision opening that is large enough to allow the tool 4 and sleeve 2 to be inserted into the cornea without allowing the irrigation fluid to leak back out of the incision. This requires making an incision that is approximately the same size as the outer diameter of the sleeve 2.

The cornea tissue tends to deflect the rubber sleeve wall when there is a minimal clearance between the incision and the outer surface of the sleeve. Deflection of the sleeve wall may create frictional contact between the inner surface of the sleeve and the oscillating tip. The frictional contact between the sleeve and the tip creates heat. The wall deflection also restricts the flow of irrigation fluid and reduces the heat transfer rate into the fluid. The heat can raise the temperature of the sleeve to a level that burns the endothelium tissue of the cornea. Damage to the endothelium tissue of the cornea is irreversible. It is therefore very important to avoid corneal burning during a phaco procedure.

There have been developed irrigation sleeves that are constructed from a rigid material such as metal or TEFLON.

The rigid material prevents the sleeve from collapsing and generating heat. Unfortunately, the rigid sleeves may damage the cornea when the tool and sleeve are repeatedly pulled in and out of the incision. It would be desirable to provide an irrigation sleeve for an ultrasonically driven surgical instrument which does not collapse, is flexible enough to be repeatedly pulled through an incision, and has a low coefficient of friction to prevent a rolling of Decemets membrane.

SUMMARY OF THE INVENTION

The present invention is an irrigation sleeve for a surgical instrument. The irrigation sleeve includes an outer band that is attached to the sleeve. The irrigation sleeve has an inner bore that extends from a proximal end to a distal end of the sleeve. Located at the distal end of the sleeve is a tip which has an outlet port. The outer band is attached to the distal end of the sleeve at a location that is adjacent to the tip.

BRIEF DESCRIPTION OF THE DRAWINGS

FIG. 1 is a side view of a surgical instrument of the prior art;

FIG. 2 is a side view of a surgical instrument of the present invention;

DETAILED DESCRIPTION OF THE INVENTION

Figure 4:
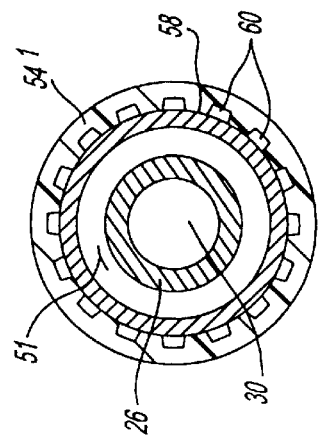
FIG. 4 is an alternate embodiment of the band.

The present invention is an irrigation sleeve for a surgical instrument which has an outer band that is attached to the sleeve. The irrigation sleeve has an inner bore that extends from a proximal end to a distal end of the sleeve. Located at the distal end of the sleeve is a tip which has an outlet port. The outer band is attached to the distal end of the sleeve at a location that is adjacent to the tip. The sleeve is typically constructed from a silicone rubber material that is flexible enough so that the tip can be repeatedly inserted through an incision in a cornea without damaging the eye. The band is preferably constructed from a rigid material such as TEFLON which will not collapse when inserted through the cornea incision. The band has a low coefficient of thermal conductivity so that heat is not transferred to the cornea tissue. The band also has a low coefficient of friction so that the Decemets membrane does not roll up on the sleeve when inserted into and out of the incision.

FIG. 2 shows a surgical instrument 20 of the present invention. The instrument 20 includes an outer shell 22 which has an inlet port 24. The inlet port 24 is connected to an irrigation line (not shown) that provides an irrigation fluid. Extending through the shell 22 is an ultrasonically driven tip 26. The tip 26 is typically oscillated by an ultrasonic driving motor (not shown) located within the shell 22 at the proximal end of the tip 26. The tip 26 transfers energy to emulsify tissue such as the lens of a cornea. The tip 26 also has an inner channel 30 that is connected to an aspiration system (not shown). The aspiration system creates a negative fluid pressure which pulls the irrigation fluid and emulsified tissue from the tip 26 through the inner channel 30 of the tip 26.

A sleeve 32 is attached to the outer shell 22. The sleeve 32 has a proximal end 34 and a distal end 36. An inner bore 38 extends from the proximal end 34 to the distal end 36 of the sleeve 32. The inner bore 38 has a major diameter which tapers to a minor diameter in the distal end 36 of the sleeve 32.

The sleeve 32 has an internal thread 40 that is screwed onto a corresponding external thread 42 of the outer shell 22. The sleeve 32 may also have an annular lip 44 that seals the sleeve 32 to the outer shell 22. The sleeve 32 may have a plurality of outer ridges 46 that increase the mechanical grip when the sleeve 32 is attached to the shell 22.

The distal end 36 of the sleeve 32 has a sleeve tip 48 which contains an outlet port 50. The outer diameter of the tip 26 is smaller than the inner diameter of the sleeve 32 so that there is an inner passage 51 which provides fluid communication between the inlet 24 and outlet 50 ports.

The tip 26 extends through a distal opening 52 in the sleeve 32. The diameter of the opening 52 is preferably the same as the outer diameter of the tip 26 so that there is an interference fit between the two components. The sleeve 32 is preferably constructed from a silicone rubber material which is flexible enough to allow the tip 26 to move in a reciprocating motion relative to the sleeve 32 while still sealing the end of the sleeve tip 48. The rubber tip 48 is also flexible enough to deflect when the tip 26 and sleeve 32 are inserted into a corneal incision to minimize damage to the corneal tissue.

Figure 3:
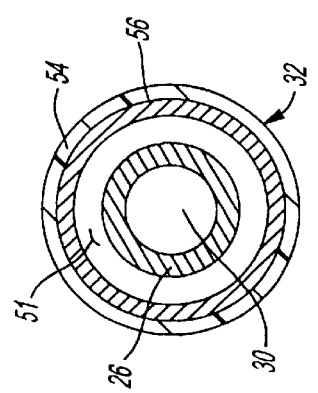
FIG. 3 is a cross-sectional view of a band of the instrument.

Referring to FIGS. 2 and 3, an outer band 54 is attached to the distal end 36 of the sleeve 32 at a location that is adjacent to the rubber tip 48. The outer band 54 is preferably inserted into an outer annular groove 56 of the sleeve 32 so that there is not a discontinuity in the sleeve outer surface.

In one embodiment, the outer band 54 is constructed from a TEFLON material. TEFLON has a coefficient of friction that is lower than the rubber so that the outer surface of the band 54 does not roll up the Decemets membrane of the cornea when the sleeve is pulled through the incision. The TEFLON also has a stiffness that is greater than the rubber sleeve 32. The TEFLON outer band 54 thus provides structural rigidity which prevents the sleeve 32 from collapsing and generating frictional heat. Additionally the TEFLON outer band 54 has a lower coefficient of thermal conductivity than the rubber sleeve 32 to minimize the amount of heat that is transferred from the sleeve 32 to the cornea.

FIG. 4 shows an alternate embodiment of an outer band 54' which has a plurality of inner ridges 58. The inner ridges 58 create air gaps 60 between the sleeve 32 and the outer band 54'. The air gaps 60 further reduce the rate of heat transfer from the sleeve 32 to the cornea.

Figure 5:
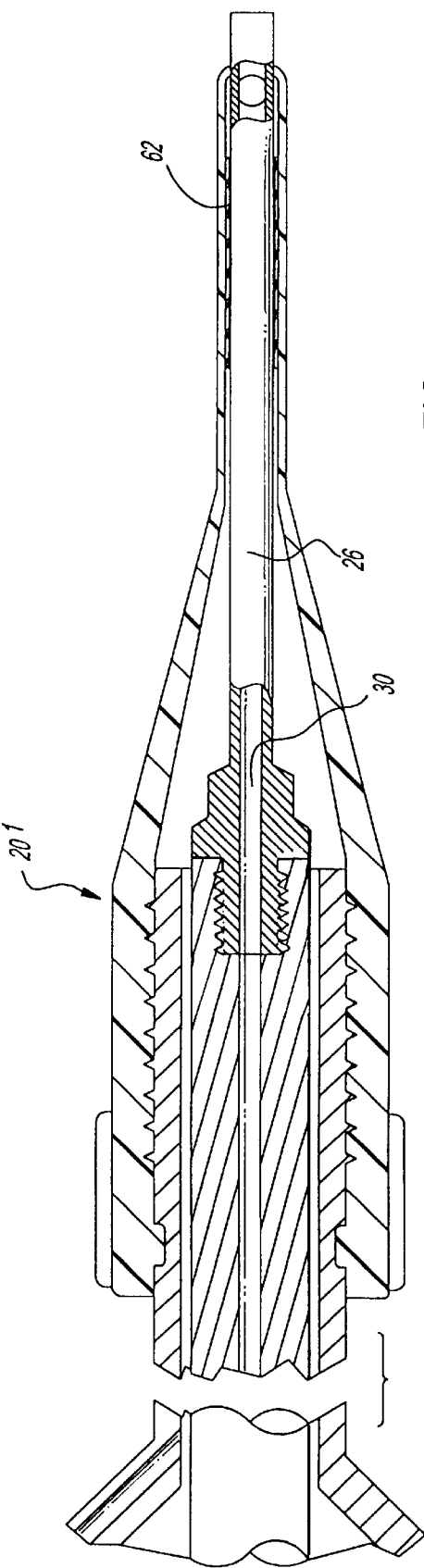
FIG. 5 is an alternate embodiment of the instrument.

FIG. 5 shows an alternate embodiment of a surgical instrument 20' which has an inner band 62 that is attached to the sleeve 32. The inner band 62 can be used with or without an outer band. The inner band 62 may be constructed from TEFLON to increase the structural rigidity and decrease the coefficient of thermal conductivity of the sleeve. The inner band 62 may also trap air bubbles that migrate down the inner passage 51 from the inlet port 24. The inner band 62 may have outer ridges (not shown) that create air gaps similar to the embodiment shown in FIG. 4.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An irrigation sleeve for a medical instrument, comprising:

a sleeve that has an inner bore which extends from a proximal end to a distal end of said sleeve, said distal end of said sleeve having a tip that has an outlet port which is in fluid communication with said inner bore, said tip having a groove; and, a thermally non-conductive outer band that is located within said groove of said sleeve, said outer band having a plurality of ridges which create a plurality of air gaps between said sleeve and said outer band.

2. The irrigation sleeve as recited in claim 1, wherein said outer band has a stiffness that is greater than a stiffness of said sleeve.

3. The irrigation sleeve as recited in claim 2, wherein said outer band has a coefficient of friction that is less than a coefficient of friction of said sleeve.

4. The irrigation sleeve as recited in claim 1, wherein said outer band has a coefficient of friction that is less than a coefficient of friction of said sleeve.

5. The irrigation sleeve as recited in claim 1, wherein said outer band has a coefficient of thermal conductivity that is less than a coefficient of thermal conductivity of said sleeve.

6. The irrigation sleeve as recited in claim 1, further comprising an inner band that is attached to said distal end of said sleeve.

7. The irrigation sleeve as recited in claim 6, wherein said outer band has a coefficient of thermal conductivity that is less than a coefficient of thermal conductivity of said sleeve.

8. A surgical instrument, comprising:

a sleeve that has an inner bore which extends from a proximal end to a distal end of said sleeve, said distal end of said sleeve having a tip that has a distal opening and an outlet port which is in fluid communication with said inner bore, said tip having a groove;

a thermally non-conductive outer band that is located within said groove of said sleeve, said outer band having a plurality of ridges which create a plurality of air gaps between said sleeve and said outer band;

a shell that is attached to said proximal end of said sleeve, said shell having an inlet port; and, a tip that extends through said inner bore of said sleeve and through said distal opening, wherein said tip and sleeve define an inner passage that provides fluid communication between said inlet port and said outlet port.

9. The surgical instrument as recited in claim 8, wherein said distal opening has a diameter equal to a diameter of said tip.

10. The surgical instrument as recited in claim 8, wherein said outer band has a stiffness that is greater than a stiffness of said sleeve.

11. The surgical instrument as recited in claim 8, wherein said outer band has a coefficient of friction that is less than a coefficient of friction of said sleeve.

12. The surgical instrument as recited in claim 8, wherein said outer band has a coefficient of thermal conductivity that is less than a coefficient of thermal conductivity of said sleeve.

* * * * *